(12) United States Patent
Egi et al.

(10) Patent No.: US 6,242,015 B1
(45) Date of Patent: Jun. 5, 2001

(54) PROCESS FOR PRODUCING A FRUITY FLAVORING AGENT

(75) Inventors: Makoto Egi, Tokyo; Atsuko Hazama, Matsudo; Nobuo Ogata, Tsuchiura; Shigenori Ohta, Komae, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 08/973,517

(22) PCT Filed: Jun. 7, 1996

(86) PCT No.: PCT/JP96/01554

§ 371 Date: Dec. 5, 1997

§ 102(e) Date: Dec. 5, 1997

(87) PCT Pub. No.: WO96/41854

PCT Pub. Date: Dec. 27, 1996

(30) Foreign Application Priority Data

Jun. 8, 1995 (JP) ................................. 7-141586

(51) Int. Cl.$^7$ ....................................... A23C 9/12
(52) U.S. Cl. .......................... 426/34; 426/35; 426/534; 426/650
(58) Field of Search .................. 426/33, 34, 35, 426/36, 37, 38, 39, 42, 43, 534, 650

(56) References Cited

U.S. PATENT DOCUMENTS

| 3,469,993 | 9/1969 | Pangier et al. ............. 99/59 |
| 3,650,768 | 3/1972 | Roberts ....................... 99/116 |
| 4,065,580 | * 12/1977 | Feldman et al. .............. 426/33 |

FOREIGN PATENT DOCUMENTS

| 45-3187 | 2/1970 | (JP) . |
| 51-61673 | 5/1976 | (JP) . |
| 56-50554 | 11/1981 | (JP) . |
| 59-66856 | 4/1983 | (JP) . |
| 4-346746 | 4/1993 | (JP) . |
| 09681 | 5/1993 | (WO) . |

OTHER PUBLICATIONS

M.C.S. Reddy, Section B, The Sciences and Engineering, vol. 31, No. 2, 1970, pp. 744–745.
M.E. Morgan, Biotechnology and Bioengineering, vol. 18, No. 7, 1976, pp. 953–965.
Nippon Shokuhin Kogyo Gakkaishi, vol. 30, No. 10 (1983) 572–578.

* cited by examiner

Primary Examiner—Leslie Wong
(74) Attorney, Agent, or Firm—Fitzpatrick, Cella, Harper & Scinto

(57) ABSTRACT

The present invention relates to a process for producing a flavoring agent, which includes treating milk or milk products with lipase, and in the presence of an alcohol, with an animal-derived enzyme which has the activity of forming an ester from an organic acid and an alcohol (hereinafter referred to as an ester-synthesizing enzyme). A flavoring agent having a rich fruity flavor can be produced by using, as the ester-synthesizing enzyme, an enzyme which has the ethyl butyrate-synthesizing activity of 0.1 unit/mg protein or above when 0.5% (w/w) ethanol and 2.6% (w/w) butyric acid are used as substrates. The flavoring agent according to the present invention is useful in processing not only milk products but also various foods.

13 Claims, No Drawings

PROCESS FOR PRODUCING A FRUITY FLAVORING AGENT

This application is a National Stage Filing of PCT/JP96/01554.

TECHNICAL FIELD

The present invention relates to a process for producing a flavoring agent having a strong fruity flavor which comprises treating milk or milk products with lipase and an ester-synthesizing enzyme, and to a use of said flavoring agent in foods, particularly processed foods.

BACKGROUND ART

Some methods are known for producing flavoring agents derived from milk or milk products: for example, a method in which fresh cream or milk is treated with an enzyme derived from animal pharynx (U.S. Pat. Nos. 3,469,993, 3,650,768); a method in which milk or cream is treated with lipase derived from a microorganism (Japanese Published Examined Patent Application No. 3187/70); a method in which butter is hydrolyzed and then treated with lipase derived from a microorganism in the presence of an alcohol [Journal of the Japanese Society for Food Science and Technology, Vol. 30, p. 572 (1983)]; a method in which vegetable fats and oils are hydrolyzed and then treated with lipase derived from a microorganism in the presence of an alcohol (Japanese Published Examined Patent Application No. 50554/81); and a method in which butter oil is treated with esterase derived from an animal in the absence of an alcohol and then treated with lipase (Japanese Published Unexamined Patent Application No. 66856/84). The flavoring agents derived from milk or milk products which are obtained by the above methods have a butter flavor or a cheese flavor, but do not have a rich fruity flavor.

It is known that large amounts of higher fatty acid ethyl esters are formed by treating, in the presence of ethanol, butter fat with lipase derived from a microorganism [Journal of the Japanese Society for Food Science and Technology, Vol. 30, p. 572 (1983)]. However, flavoring agents containing quantities of higher fatty acid alkyl esters have waxy smell and taste.

In another known method, an enzyme derived from animal liver or kidney having a high ester-synthesizing activity is brought into contact with foods and beverages to impart a fruit flavor thereto (WO 93/09681). However, the treatment of milk or milk products with only escerase derived from animal liver or kidney would produce rather grassy smell than a fruit flavor.

DISCLOSURE OF THE INVENTION

According to the present invention, flavoring agents having a fruity flavor can be produced by treating milk or milk products with lipase, and in the presence of an alcohol, with an animal-derived enzyme having the activity to produce an ester using an organic acid and an alcohol as substrates (hereinafter referred to as an ester-synthesizing enzyme or esterase).

Preferred flavoring agents with a rich flavor can be obtained by the use of an ester-synthesizing enzyme having the ethyl butyrate-synthesizing activity of 0.1 unit/mg protein or above when 0.5% ethanol and 2.6% butyric acid are used as substrates. The enzymatic treatment may be carried out first with lipase and then with an ester-synthesizing enzyme, or with both of them at the same time.

A fermentation step with a lactic acid bacterium may be added at any stage of the production process of the above flavoring agents to intensify the flavor thereof.

The flavoring agents obtained according to the above method contain milk fat and quantities of fatty acid alkyl esters, specifically large amounts of lower fatty acid alkyl esters. They have a rich flavor and are useful in processing foods.

Of the flavoring agents obtained according to the method of the present invention, those which contain fatty acid alkyl esters in the total amount of 20 $\mu$mol or more, preferably 27 $\mu$mol or more per gram, and in which 80% or more, preferably 90% or more of the fatty acid alkyl esters contained is lower fatty acid alkyl esters have particularly rich flavor.

Specifically, flavoring agents containing lower fatty acid alkyl esters of the following composition have a rich flavor:
composition by concentration: ethyl butyrate, 35–50%, preferably 38–46%; ethyl caproate, 15–30%, preferably 20–27%; ethyl caprylate, 5–10%, preferably 6–9%; ethyl caprate, 15–30%, preferably 20–26%;
composition by weight: ethyl butyrate, 20–40 parts by weight, preferably 25–35 parts by weight; ethyl caproate, 15–30 parts by weight, preferably 20–25 parts by weight; ethyl caprylate, 3–15 parts by weight, preferably 5–10 parts by weight; ethyl caprate, 20–40 parts by weight, preferably 25–35 parts by weight.

Based on the analysis of the flavoring agents obtained by the enzyme reaction, the composition of mixtures of milk fat and fatty acid alkyl esters can be clarified, and thus the flavoring agents can be obtained only by mixing components without the enzyme reaction. However, flavoring agents obtained by the enzyme reaction have a richer flavor and are preferred.

In producing such mixtures, either saturated fatty acids or unsaturated fatty acids can be used as the fatty acid moieties of the fatty acid alkyl esters so long as they are constituents of milk fat.

In the present invention, the term lower fatty acids refers to fatty acids having 1–10 carbon atoms, and the term higher fatty acids refers to fatty acids having 11–32 carbon atoms.

Examples of the lower fatty acids which are constituents of milk fat are butyric acid, caproic acid, caprylic acid, and capric acid.

Examples of the higher fatty acids which are constituents of milk fat are lauric acid, myristic acid, pentadecylic acid, palmitic acid, palmitoleic acid, heptadecylic acid, stearic acid, oleic acid, linoleic acid, linolenic acid, arachidic acid, arachidonic acid, behenic acid, and lignoceric acid.

Examples of the alkyl moieties of the fatty acid alkyl esters are straight-chain or branched alkyl having 1–6 carbon atoms such as methyl, ethyl, propyl, isopropyl, butyl, isobutyl, sec-butyl, tert-butyl, pentyl, neopentyl, and hexyl.

Examples of the raw milk for the milk and milk products used in the present invention are those from animals such as cows, goats, sheep, camels, reindeers, yaks, horses, and donkeys.

The term milk products means the products obtained by processing milk, and examples thereof are cream, butter, butter oil, cheese, concentrated whey, ice cream, ice cream [milk solid non fat (MSNF): over 10%, fat: over 3%)], ice cream (MSNF: over 3%), concentrated milk, defatted concentrated milk, nonfat condensed milk, nonsugar skim milk, condensed milk, condensed skim milk, whole dry milk, skim milk powder, cream powder, whey powder, sweetened dry milk, sweetened skim milk powder, adjusted dry milk, yogurt (fermented milk), lactic acid beverages, and milk beverages. They are used alone or as a mixture. Solid components such as dry milk can be used in the form of a solution or a dispersion in a solvent such as milk or water.

In the enzyme reaction, the milk fat is usually used at a concentration of 3–55%, preferably 18–45%.

As for the components of general milk or milk products, it is known that whole milk comprises about 3% each of fat and protein, about 5% of sugar, and 88% of water, cheese comprises 27–34% of fat, 25–31% of protein, and 33–40% of water, and butter comprises 81–84% of fat and 16% of water. The other components of the above milk products and the main components of other milk and milk products are also widely known [Food Additives & Food Ingredients Convenient Book, edited by Akio Sotoyama, The Food Science Co., Ltd. (1976)].

The milk fat content of milk or milk products can be determined according to an ordinary method, for example, the Röse-Gottlieb method [Official Methods of Analysis of the AOAC. 13th ed. 245 (1980)].

Preferred examples of the raw materials are milk, cream, whole fat sugarless yogurt, ice cream, ice cream (MSNF: over 10%, fat: over 3%), whole dry milk, adjusted dry milk, and cheese. Particularly preferred is cream.

Suitable cream to be used includes the following: fresh cream which is prepared by separating raw milk into cream and skim milk by centrifugation; fresh cream which is prepared by adding skim milk to fresh cream to adjust the milk fat content; compound cream which is prepared by replacing a part of the milk fat contained in fresh cream by animal oils other than milk fat or vegetable oils, and then adding an emulsifier and a stabilizer thereto; and fermented cream (sour cream) which is obtained by subjecting fresh cream optionally supplemented with nonfat milk solid, rennet, or gelatin to lactic acid fermentation.

As the lipase, any of the purified enzyme, crude enzyme, and enzyme-containing substances such as microorganism culture, microbial cells or treated-matters thereof, and animal or plant cells, tissues or treated-matters thereof can be used as long as it has the triacylglycerol hydrolase (EC 3.1.1.3) activity.

Examples of the treatment means to obtain the above treated-matters are drying, freeze-drying, treatment with surfactants, enzymatic treatment, ultrasonication, mechanical friction, and protein fractionation.

As the lipase, commercially available enzyme preparations derived from various kinds of microorganisms may be used.

Examples of such enzyme preparations are Lipase M (trademark, Amano Pharmaceutical Co., Ltd., from *Mucor javanicus*), Palatase M (trademark, Novo Nordisk A/S, from *Mucor miehei*), Lipase F (trademark, Amano Pharmaceutical Co., Ltd., from Rhizopus sp.), Talipase (trademark, Tanabe Seiyaku Co., Ltd., from *Rhizopus delemar*), Neurase F (trademark, Amano Pharmaceutical Co., Ltd., from *Rhizopus niveus*), Lipase MY (trademark, Meito Sangyo Co., Ltd., from *Candida cylindracea*), Lipase A (trademark, Amano Pharmaceutical Co., Ltd., from *Aspergillus niger*), Lipase Au (trademark, Shin Nihon Chemical Co., Ltd., from *Arthrobacter ureafaciens*), Lipase P (trademark, Amano Pharmaceutical Co., Ltd., from Pseudomonas sp.), and Lipase SP (trademark, Toyo Jozo Co., Ltd., from *Chromobacterium viscosum*).

As the lipase derived from animals, commercially available enzyme preparations such as PANCREATIC LIPASE 250 (trademark, Kyowa Solzyme Co., Ltd., from pig pancreas), Lipase 400 (trademark, Kyowa Hi Foods Co., Ltd., from sheep and goat pharynx), and Lipase 600 (trademark, Kyowa Hi Foods Co., Ltd., from cow pharynx) are preferably used.

The amount of lipase to be used depends upon the kind of milk or milk products, the reaction conditions, and the content of fatty acid alkyl esters expected as flavoring agent. However, lipase derived from a microorganism may be normally added in an amount of 1–1000, preferably 10–500 units/kg of milk or milk products, and lipase derived from animal pharynx may be normally added in an amount of 10–10000, preferably 100–5000 units/kg of milk or milk products.

The enzyme activity of lipase derived from a microorganism is expressed in unit, one unit being defined as the amount of the enzyme which produces 1 $\mu$mol of fatty acid in one minute when the enzyme activity is determined according to the method described in Journal of Japan Oil Chemists' Society, Vol. 36, p. 821 (1987).

The enzyme activity of the lipase source derived from animal pharynx is determined in the following manner. A 4% solution of polyvinyl alcohol containing 25% tributyrin (hereinafter referred to as tributyrin emulsion) (1 ml) is mixed with 2 ml of McIlvain buffer (pH 5.5). To the obtained mixture is added 2 ml of an enzyme solution, and the resulting mixture is subjected to reaction at 30° C. for 60 minutes. Then, 5 ml of an ethanol-acetone mixture (1:1) is added thereto to stop the reaction. After the reaction is completed, the reaction mixture is titrated with a 0.05 N aqueous solution of sodium hydroxide using phenolphthalein as an indicator, and the enzyme activity is calculated. The enzyme activity determined by this method is expressed in unit, one unit being defined as that amount of the enzyme which produces 1 $\mu$mol of butyric acid in one minute.

The reaction is carried out by adding lipase to milk or milk products and allowing the mixture to stand at 10–45° C., preferably 20–40° C., at pH 2–8, preferably pH 3–7, ordinarily for 2–120 hours, preferably 10–72 hours.

After the reaction is completed, the obtained lipase-treated matter is treated with an ester-synthesizing enzyme in the presence of an alcohol. If necessary, lipase remaining in the lipase-treated matter may be inactivated by heating prior to the ester-synthesizing enzyme treatment.

As the alcohol, alcohols such as methyl alcohol, ethyl alcohol, propyl alcohol, isopropyl alcohol, butyl alcohol, isobutyl alcohol, sec-butyl alcohol, tert-butyl alcohol, amyl alcohol, isoamyl alcohol, and hexyl alcohol, fusel oil, etc. may be used. Preferred are ethyl alcohol and fusel oil which are ordinarily used in food products and liquors. Alcohol is used at a concentration of 0.1–20%, preferably 1–15% in the reaction mixture.

As the ester-synthesizing enzyme, any enzyme can be used as long as it is derived from an animal and has the activity to produce ester in the presence of an organic acid and an alcohol.

Typical organic acids are carboxylic acids such as fatty acids. As the ester-synthesizing enzymes are enzymes which produce esters from said carboxylic acids and alcohols, it is preferred to use esterase (EC 3.1).

Particularly preferred are enzymes which have the ethyl butyrate-forming activity of 0.1 unit/mg protein or above when used in the reaction using ethanol (0.5%) and butyric acid (2.6%) as substrates. For example, the enzyme described in WO 93/09681 is preferably used.

As the enzyme, any of the purified enzyme, crude enzyme, and cells, tissue or treated-matters thereof can be used. Examples of the treatment means to obtain the above treated-matters are drying, freeze-drying, treatment with surfactants, enzymatic treatment, ultrasonication, mechanical friction, and protein fractionation.

Specific examples of the ester-synthesizing enzymes are esterase derived from organs such as liver, kidney, and heart of animals such as cow, pig, horse, and goat. Preferred is carboxylesterase (EC 3.1.1.1).

The method for preparing esterase from animal organs varies depending upon the kind of organ or the purity of the desired enzyme, etc. For example, a crude enzyme solution can be prepared from liver in the following manner.

To minced liver is added a buffer (pH 6–7) containing sucrose, and the mixture is homogenized and then centrifuged. The obtained supernatant is adjusted to pH 4.5–5.5 with an acid such as acetic acid or hydrochloric acid and then centrifuged to obtain a precipitate. This precipitate is defatted with an organic solvent such as acetone and suspended in a buffer (pH 6–7). To the resulting suspension is added ammonium sulfate to 70% saturation, followed by centrifugation. The obtained precipitate is suspended in 3.2 M ammonium sulfate to obtain a crude enzyme solution.

The ester-synthesizing enzyme is usually used in an amount of 0.0001–10 units/kg, preferably 0.1–50 units/kg, more preferably 1–10 units/kg of milk or milk products, though the amount varies with the kind of enzyme, the kind of milk or milk products, the reaction conditions, and the content of fatty acid alkyl esters expected as flavoring agent.

The enzyme activity of the ester-synthesizing enzyme is determined in the following manner. To 1.9 ml of 0.1 M phosphate buffer (pH 6) containing 0.5% ethanol and 2.6% butyric acid is added 0.1 ml of an enzyme solution. The mixture is subjected to reaction at 30° C. for 10 minutes, followed by addition of 1.0 ml of acetone to stop the reaction. After the reaction is completed, 2.0 ml of an ether solution containing 50 $\mu$M ethyl caproate as an internal standard substance is added to the reaction mixture, followed by centrifugation at 3000×g for 10 minutes. Then, the amount of ethyl butyrate in the supernatant is determined by gas chromatography. Separately, 0.1 ml of the same enzyme solution is added to 1.9 ml of the same substrate solution previously mixed with 1 ml of acetone, and the resulting mixture is treated in the same manner as above to obtain the blank value. The enzyme activity is calculated from the difference between the obtained values which is regarded as the amount of ethyl butyrate produced in the reaction mixture. The enzyme activity determined according to the above method is expressed in unit, one unit being defined as that amount of the enzyme which produces 1 $\mu$mol of ethyl butyrate in one minute.

The reaction is carried out by adding an alcohol and the ester-synthesizing enzyme to the lipase-treated milk or milk products and allowing the mixture to stand at 10–60° C., preferably 20–50° C., at pH 3–8, preferably pH 4–7, usually for 2–120 hours, preferably 10–72 hours; or by adding an alcohol, lipase, and the ester-synthesizing enzyme to milk or milk products and allowing the mixture to stand under the same conditions as above.

After the reaction is completed, the obtained lipase and ester-synthesizing enzyme-treated milk or milk products can be used as the flavoring agent as such or after inactivation of lipase and esterase in the product by heating.

The process for producing a flavoring agent according to the present invention may further comprise fermenting milk, milk products, or lipase- or esterase-treated products thereof using a lactic acid bacterium.

Examples of the lactic acid bacteria are microorganisms belonging to the genus Streptococcus, Lactobacillus, Lactococcus, Pediococcus, Leuconostoc, or Bifidobacterium. Preferred are those belonging to *Streptococcus thermophilus, Lactobacillus bulgaricus, L. helveticus, L. jugurti*, or *L. acidophilus*.

The fermentation is carried out by adding the lactic acid bacterium to milk, milk products, or the lipase- or esterase-treated products thereof in an amount of 0.01–1% (w/w) by wet cell weight, and then subjecting the resulting mixture to reaction at 10–50° C., preferably 20–45° C., for 2–120 hours, preferably 10–72 hours.

After the reaction is completed, the lactic acid bacterium-treated product, as such or after killing the lactic acid bacterium remaining in the product, is used to prepare the flavoring agent or is used as the flavoring agent.

The fermentation product may be used as the flavoring agent as such or mixed with a flavoring material, a blender, a modifier, an adjuvant, a fixative, etc.

Examples of the flavoring materials are natural flavoring materials such as purified oil, oleo-resin, recovered flavor, and products extracted or isolated from natural sources, and synthetic flavoring materials such as ester, alcohol, aldehyde, ketone, and lactone.

The flavoring agent of the present invention is added in the course of process of preparing, processing or cooking food products such as agricultural products, fermented products, livestock products, and marine products.

Examples of the agricultural products are bread such as one-loaf bread and buns, noodles such as Japanese noodles, Chinese noodles, spaghetti, and macaroni, confectionery such as biscuits, chocolates, candies, chewing gum, snacks, cakes, Japanese cakes, cake mix, and ices, vegetable fats and oils such as margarine, shortening, and lard, and soybean protein products such as bean curd (tofu), soy milk, and those containing defatted soybean, and granular soybean protein.

Examples of the fermented products are alcoholic beverages such as liqueur, sauce, soy sauce, bean paste (miso), and pickles.

Examples of the livestock products are milk products, meat products such as ham, sausage, and bacon, and egg products such as mayonnaise and dressing.

Examples of the marine products are fish paste products such as steamed fish paste, baked fish paste, and fish meat sausage.

BEST MODE FOR CARRYING OUT THE INVENTION

Examples, Comparative Examples, and Reference Examples are given below.

EXAMPLE 1

To 100 g of fresh cream containing 35% fat was added 130 units of Lipase Powder 600 (trademark, Kyowa Hi Foods Co., Ltd., lipase from cow pharynx), followed by thorough mixing. The mixture was hydrolyzed at 38° C. for 72 hours and the obtained hydrolyzate was heated at 90° C. for 60 minutes to inactivate the lipase. To the obtained mixture were added 5 ml of ethanol and 0.7 unit of the esterase derived from pig liver obtained in Reference Example 1, followed by thorough mixing with stirring. Then, the mixture was subjected to reaction at 40° C. for 72 hours.

After the reaction was completed, the mixture was heated at 80° C. for 30 minutes to inactivate the esterase, whereby a flavoring agent was obtained. Sensory evaluation was carried out on the obtained flavoring agent in respect of cheese flavor and fruit flavor by 15 trained panelists. The flavors were evaluated into 6 grades of 0 point (no flavor) to 5 points (strong flavor), and the average values were calculated.

The average values for the cheese flavor and the fruit flavor were 0 point and 4.8 points, respectively.

EXAMPLE 2

The same procedure as in Example 1 was repeated, except that the esterase derived from pig liver was replaced by 0.7 unit of the esterase derived from pig kidney obtained in Reference Example 2, to obtain a flavoring agent. Sensory evaluation made on the obtained flavoring agent gave the average values of 0 point and 4.8 points respectively for the cheese flavor and the fruit flavor.

EXAMPLE 3

The same procedure as in Example 1 was repeated, except that the esterase derived from pig liver was replaced by 0.7 unit of the esterase derived from cow liver obtained in Reference Example 3, to obtain a flavoring agent. Sensory evaluation made on the obtained flavoring agent gave the average values of 0 point and 4.5 points respectively for the cheese flavor and the fruit flavor.

EXAMPLE 4

The same procedure as in Example 1 was repeated, except that the esterase derived from pig liver was replaced by 0.7 unit of the esterase derived from cow kidney obtained in Reference Example 4, to obtain a flavoring agent. Sensory evaluation made on the obtained flavoring agent gave the average values of 0 point and 4.4 points respectively for the cheese flavor and the fruit flavor.

EXAMPLE 5

The same procedure as in Example 1 was repeated, except that Lipase Powder 600 (trademark, lipase from cow pharynx) was replaced by 10 units of Lipase MY (trademark, Meito Sangyo Co., Ltd., lipase derived from *Candida cylindracea*), to obtain a flavoring agent. Sensory evaluation made on the obtained flavoring agent gave the average values of 0 point and 4.9 points respectively for the cheese flavor and the fruit flavor.

EXAMPLE 6

The same procedure as in Example 1 was repeated, except that Lipase Powder 600 (trademark, lipase from cow pharynx) was replaced by 10 units of Palatase M (trademark, Novo Nordisk A/S, lipase derived from *Mucor miehei*), to obtain a flavoring agent. Sensory evaluation made on the obtained flavoring agent gave the average values of 0 point and 4.5 points respectively for the cheese flavor and the fruit flavor.

EXAMPLE 7

The same procedure as in Example 1 was repeated, except that 5 ml of ethanol was replaced by 5 ml of fusel oil, to obtain a flavoring agent. Sensory evaluation made on the obtained flavoring agent gave the average values of 0 point and 4.8 points respectively for the cheese flavor and the fruit flavor.

EXAMPLE 8

To 100 g of fresh cream having the fat content adjusted to 35% was added 0.1 g of TR 160 (trademark, Kyowa Hi Foods Co., Ltd., frozen cells of *Lactobacillus bulgaricus*), and the mixture was cultured at 37° C. for 48 hours. To the resulting culture was added 130 units of Lipase Powder 600 (trademark, lipase derived from cow pharynx), followed by thorough mixing. The mixture was hydrolyzed at 38° C. for 72 hours and then heated at 90° C. for 60 minutes to inactivate the lipase. To the resulting hydrolyzate were added 5 ml of ethanol and 0.7 unit of the esterase derived from pig liver obtained in Reference Example 1. The mixture was stirred well and then subjected to reaction at 40° C. for 72 hours. After the reaction was completed, the mixture was heated at 80° C. for 30 minutes to inactivate the esterase, whereby a flavoring agent was obtained.

Sensory evaluation made on the obtained flavoring agent in the same manner as in Example 1 gave the average values of 0 point and 4.4 points respectively for the cheese flavor and the fruit flavor.

EXAMPLE 9

The same procedure as in Example 8 was repeated, except that TR 160 was replaced by 0.1 g of LBST (trademark, Kyowa Hi Foods Co., Ltd., frozen cells of *Lactobacillus helveticus* and *Streptococcus thermophilus*), to obtain a flavoring agent. Sensory evaluation made on the obtained flavoring agent gave the average values of 0 point and 4.8 points respectively for the cheese flavor and the fruit flavor.

EXAMPLE 10

To 0.1 g of the flavoring agent obtained in Example 8 was added 5 ml of acetone containing 40 $\mu$m ethyl caproate and 40 $\mu$M ethyl myristate as internal standards, and the fatty acid ethyl ester content of the flavoring agent was determined by gas chromatography.

The results are shown in Table 1.

TABLE 1

| Fatty acid ethyl ester | Concentration ($\mu$mol/g) | Composition by concentration (%) | Composition by weight (%) |
| --- | --- | --- | --- |
| Ethyl butyrate | 30.5 | 38.5 | 28.1 |
| Ethyl caproate | 17.6 | 22.2 | 20.1 |
| Ethyl caprylate | 6.3 | 7.9 | 8.6 |
| Ethyl caprate | 19.1 | 24.1 | 30.4 |
| Ethyl laurate | 1.4 | 1.8 | 2.5 |
| Ethyl myristate | 1.1 | 1.4 | 2.2 |
| Ethyl palmitate | 0.7 | 0.1 | 1.6 |
| Ethyl stearate | 1.8 | 2.3 | 4.5 |
| Ethyl oleate | 0.7 | 0.9 | 1.7 |
| Ethyl linoleate | 0.1 | 0.1 | 0.2 |

As clear from Table 1, 92% of the whole fatty acid alkyl esters in this flavoring agent was lower fatty acid ethyl esters (ethyl butyrate, ethyl caproate, ethyl caprylate, and ethyl caprate) and thus the main component of the fruit flavor was lower fatty acid ethyl esters.

EXAMPLE 11

The flavoring agent prepared in Example 8 (2 g), 200 g of granulated sugar, 200 g of whole eggs, 80 g of water, and 10 g of HI-UP Miyoshi-Oil (trademark, Miyoshi Oil Co., Ltd., foaming agent) were mixed together using Hobart mixer at the low speed for 2 minutes and at the medium speed for 10 seconds. To the resulting mixture was added 200 g of Heart flour (trademark, Nippon Flour Mills Co., Ltd., flour), followed by mixing at the low speed for 2 minutes. Then, the mixture was whipped at the medium speed until the specific gravity thereof become 0.42. The obtained dough (250 g) was put in a cake mold and baked at 180° C. for 35 minutes to give a sponge cake having a desirable fruit flavor.

EXAMPLE 12

The same procedure as in Example 1 was repeated, except that the fresh cream containing 35% fat was replaced by fresh cream containing 18% fat, to obtain a flavoring agent. Sensory evaluation was made on the obtained flavoring agent by 15 panelists. The average values for the cheese flavor and the fruit flavor were 0 point and 3.0 points, respectively.

To 0.1 g of the obtained flavoring agent was added 5 ml of acetone containing 40 $\mu$M ethyl caproate and 40 $\mu$M ethyl myristate as internal standards, and the fatty acid ethyl ester content per gram of the flavoring agent was determined by gas chromatography as well as the composition by concentration and the composition by weight of the fatty acid ethyl esters.

The results are shown in Table 2.

TABLE 2

| Fatty acid ethyl ester | Concentration ($\mu$mol/g) | Composition by concentration (%) | Composition by weight (%) |
|---|---|---|---|
| Ethyl butyrate | 13.2 | 45.4 | 34.8 |
| Ethyl caproate | 6.5 | 22.3 | 21.3 |
| Ethyl caprylate | 2.0 | 6.8 | 7.8 |
| Ethyl caprate | 6.2 | 21.3 | 28.2 |
| Ethyl laurate | 0.2 | 0.7 | 1.0 |
| Ethyl myristate | 0.1 | 0.3 | 0.6 |
| Ethyl palmitate | 0.2 | 0.7 | 1.3 |
| Ethyl stearate | 0.5 | 1.7 | 3.6 |
| Ethyl oleate | 0.2 | 0.7 | 1.4 |
| Ethyl linoleate | 0.0 | 0.0 | 0.0 |

As shown in Table 2, 95.9% of the whole fatty acid ethyl esters was lower fatty acid ethyl esters.

EXAMPLE 13

The same procedure as in Example 1 was repeated, except that the fresh cream containing 35% fat was replaced by fresh cream containing 45% fat, to obtain a flavoring agent. Sensory evaluation was made on the obtained flavoring agent by 15 panelists. The average values for the cheese flavor and the fruit flavor were 0 point and 4.8 points, respectively.

To 0.1 g of the obtained flavoring agent was added 5 ml of acetone containing 40 $\mu$M ethyl caproate and 40 $\mu$M ethyl myristate as internal standards, and the fatty acid ethyl ester content per gram of the flavoring agent was determined by gas chromatography as well as the composition by concentration and the composition by weight of the fatty acid ethyl esters.

The results are shown in Table 3.

TABLE 3

| Fatty acid ethyl ester | Concentration ($\mu$mol/g) | Composition by concentration (%) | Composition by weight (%) |
|---|---|---|---|
| Ethyl butyrate | 38.2 | 39.2 | 29.9 |
| Ethyl caproate | 24.2 | 24.9 | 23.5 |
| Ethyl caprylate | 8.0 | 8.2 | 9.3 |
| Ethyl caprate | 24.5 | 25.2 | 33.1 |
| Ethyl laurate | 1.2 | 1.2 | 1.9 |
| Ethyl myristate | 0.2 | 0.2 | 0.4 |
| Ethyl palmitate | 0.4 | 0.4 | 0.8 |
| Ethyl stearate | 0.4 | 0.4 | 0.8 |
| Ethyl oleate | 0.1 | 0.1 | 0.2 |
| Ethyl linoleate | 0.1 | 0.1 | 0.2 |

As shown in Table 3, 97.5% of the whole fatty acid esters was lower fatty acid esters.

EXAMPLE 14

To Snow Brand New Whip (trademark, whipping cream: milk solid nonfat content 3.5%, milk fat content 20.0%, vegetable fat content 20.0%, Snow Brand Milk Products Co., Ltd.) was added the flavoring agent prepared in Example 9, 12, or 13 in an amount of 0.1%, and the mixture was whipped to prepare whipped cream.

Sensory evaluation was conducted on the whipped cream in respect of fruitiness, lightness, sweetness, sourness, and mildness by 10 trained panelists. The above qualities were evaluated into 6 grades of 0 point to 5 points, and the average values were calculated. In the grading, the fruitiness, sweetness, sourness, and mildness become weaker toward 0 point and stronger toward 5 points, and the lightness becomes heavier toward 0 point and lighter or more fragrant toward 5 points.

The results are shown in Table 4.

TABLE 4

| | Fruitiness | Lightness | Sweetness | Sourness | Mildness |
|---|---|---|---|---|---|
| Comparative Example 2 (no flavoring agents) | 0 | 2.5 | 0.2 | 2.0 | 2.5 |
| Example 12 (present inv.) | 0.2 | 4.2 | 4.0 | 0.4 | 4.2 |
| Example 9 (present inv.) | 0.8 | 4.2 | 4.5 | 0.5 | 4.2 |
| Example 13 (present inv.) | 0.8 | 4.5 | 4.5 | 0.2 | 4.0 |
| Comparative Example 3 | 0 | 0 | 0.2 | 2.0 | 2.5 |
| Comparative Example 4 | 2.2 | 0.4 | 3.0 | 4.5 | 2.5 |

TABLE 4-continued

|  | Fruiti-ness | Light-ness | Sweet-ness | Sour-ness | Mild-ness |
|---|---|---|---|---|---|
| Comparative Example 5 | 2.5 | 0.5 | 0.2 | 3.2 | 2.5 |

As clear from Table 4, the flavoring agent of the present invention is effective in preparing food products having intensified fruitiness, lightness, sweetness and mildness, and reduced sourness.

Comparative Example 1

To 100 g of fresh cream having the fat content adjusted to 35% was added 130 units of Lipase Powder 600 (trademark, lipase derived from cow pharynx), followed by thorough mixing. The mixture was hydrolyzed at 38° C. for 72 hours and then heated at 90° C. for 60 minutes to inactivate the lipase. To the resulting hydrolyzate were added 5 ml of ethanol and 0.5 unit of lipase derived from *Candida cylindracea* (Lipase MY, Kyowa Solzyme Co., Ltd.). The mixture was stirred well and then subjected to reaction at 40° C. for 72 hours. After the reaction was completed, the mixture was heated at 80° C. for 30 minutes to inactivate the lipase, whereby a flavoring agent was obtained.

Sensory evaluation made on this flavoring agent in the same manner as in Example 1 gave the average values of 4.9 points and 0.2 point respectively for the cheese flavor and the fruit flavor.

Comparative Example 2

The same procedure as in Example 14 was repeated, except that no flavoring agent was added to prepare whipped cream. Sensory evaluation was made on the obtained cream.

The results are shown in Table 4.

Comparative Examples 3–5

The same procedure as in Example 14 was repeated, except that Butter Flavor L-11 (trademark, Kyowa Hi Foods Co., Ltd., butter flavor, Comparative Example 3), Pineapple Flavor C80883 (trademark, Ogawa Koryosha, pineapple flavor, Comparative Example 4), or Banana Flavor C80880 (trademark, Ogawa Koryosha, banana flavor, Comparative Example 5) was used as the flavoring agent to prepare whipped cream. Sensory evaluation was made on the obtained cream.

The results are shown in Table 4.

Reference Example 1

After 1 kg of pig liver was minced with a mincer, 3000 ml of 0.02 M phosphate buffer (pH 6.5) was added thereto. The mixture was homogenized and then centrifuged at 10000×g for 30 minutes. The obtained supernatant was adjusted to pH 5.3 with 2 N acetic acid and allowed to stand at 4° C. for 10 hours. Then, the supernatant was centrifuged at 10000×g for 30 minutes to obtain a precipitate. To the precipitate was added 1000 ml of ice-cold acetone (−20° C. ), and the mixture was stirred and defatted by suction filtration using Toyo No. 2 filter paper. This defatting treatment with acetone was repeated three times. Then, the obtained residue was dried in a vacuum drying apparatus at 20° C. to remove the remaining acetone. To the residue was added 1000 ml of 0.05 M phosphate buffer (pH 6.7), and the mixture was stirred at 4° C. for 10 hours and then centrifuged at 10000×g for 30 minutes to obtain a supernatant. To the supernatant was added ammonium sulfate to 50% saturation, and the mixture was allowed to stand at 4° C. for 5 hours, followed by centrifugation at 10000×g for 30 minutes. After the precipitate was removed, ammonium sulfate was added to the supernatant to 70% saturation and the mixture was allowed to stand at 4° C. for 5 hours. Then, the mixture was centrifuged at 10000×g for 30 minutes, and the obtained precipitate was dissolved in 3.2 M ammonium sulfate to make a total volume of 100 ml, whereby a solution of enzyme derived from pig liver was obtained. The esterase activity of the enzyme thus prepared was 0.37 unit/mg protein.

Reference Examples 2–4

The same procedure as in Reference Example 1 was repeated, except that pig liver was replaced by pig kidney (Reference Example 2), cow liver (Reference Example 3), or cow kidney (Reference Example 4) to prepare an enzyme. The esterase activities of the obtained enzymes were as follows: enzyme derived from pig kidney, 0.35 unit/mg protein; enzyme derived from cow liver, 0.37 unit/mg protein; enzyme derived from cow kidney, 0.35 unit/mg protein.

Industrial Applicability

The flavoring agent obtained according to the method of the present invention has a rich flavor and can be used in the production of foods, particularly processed foods, to impart a fruit flavor thereto.

What is claimed is:

1. A process for producing a fruity flavoring agent containing high contents of lower fatty acid alkyl esters and low contents of higher fatty acid alkyl esters, which comprises:

treating milk or milk products with lipase to form free fatty acids;

inactivating the lipase; and treating the resultant mixture with an animal-derived esterase in the presence of an alcohol.

2. The process according to claim 1, wherein the esterase has an ethyl butyrate-synthesizing activity of at least 0.1 unit/mg protein in the presence of 0.5% (w/w) 1 and 2.6% (w/w) butyric acid substrate.

3. The process according to claim 1 or 2, further comprising a step of fermenting treatment with a lactic acid bacterium.

4. The process according to claim 1, wherein the esterase is derived from an animal selected from the group consisting of cow, pig, horse and goat.

5. The process according to claim 4, wherein the esterase is derived from the liver, kidney or heart of said animal.

6. The process according to claim 1, 2, 4 or 5, wherein the esterase is carboxylesterase.

7. The process according to claim 1, wherein said lipase is derived from an animal pharynx.

8. The process according to claim 1, wherein the milk fat concentration of the reaction mixture is 3–55% (w/w) prior to any enzyme reaction.

9. The process according to claim 1, wherein the product is cream.

10. The process according to any of claims 1, 2, 4, 5, 7 or 9, wherein the fruity flavoring agent contains fatty acid alkyl esters in an amount of at least 20 μmol per gram, and at least 80% of said fatty acid alkyl esters are lower fatty acid alkyl esters.

11. The process according to claim 10, wherein the lower fatty acid alkyl esters comprise 25–35 parts by weight of ethyl butyrate, 20–25 parts by weight of ethyl caproate, 5–10 parts by weight of ethyl caprylate, and 25–35 parts by weight of ethyl caprate.

12. The process according to claim 1, wherein the concentration of alcohol in the reaction mixture is 0.1–20%.

13. The process according to claim 1, wherein the esterase enzyme reaction is carried out at 10–60° C. for 2–120 hours.

* * * * *